United States Patent [19]

Guttmann et al.

[11] Patent Number: 4,556,731

[45] Date of Patent: Dec. 3, 1985

[54] PROCESS FOR THE OXIDATION OF OLEFINS USING CATALYSTS CONTAINING VARIOUS PROMOTER ELEMENTS

[75] Inventors: Andrew T. Guttmann, Maple Heights; Robert K. Grasselli, Chagrin Falls, both of Ohio

[73] Assignee: The Standard Oil Company, Cleveland, Ohio

[21] Appl. No.: 369,371

[22] Filed: Apr. 19, 1982

Related U.S. Application Data

[63] Continuation of Ser. No. 148,120, May 9, 1980, abandoned, which is a continuation of Ser. No. 819,733, Jul. 9, 1977, abandoned.

[51] Int. Cl.$^4$ .................. C07C 45/35; C07C 47/22; C07C 51/25; C07C 57/05
[52] U.S. Cl. .................. 562/546; 502/205; 502/206; 502/211; 502/212; 502/215; 502/241; 502/242; 502/243; 502/302; 502/304; 502/306; 502/308; 502/310; 502/311; 502/314; 502/315; 502/316; 502/317; 502/318; 502/319; 562/545; 562/547; 568/477; 568/478; 568/479; 568/480
[58] Field of Search .................. 562/546; 260/413; 568/477, 479, 480, 478; 502/308, 311

[56] References Cited

U.S. PATENT DOCUMENTS

| 3,118,927 | 1/1964 | Foster | 562/545 |
|---|---|---|---|
| 3,446,840 | 5/1969 | Kato et al. | 562/545 |
| 3,527,797 | 9/1970 | Krabetz et al. | 562/545 |
| 3,642,930 | 2/1972 | Grasselli et al. | 562/545 |
| 3,825,502 | 7/1974 | Takenaka et al. | 562/545 |
| 3,894,091 | 7/1975 | Sakakibara et al. | 562/545 |
| 3,956,181 | 5/1976 | Grasselli et al. | 562/545 |
| 3,968,165 | 7/1976 | Ono et al. | 562/545 |
| 3,968,166 | 7/1976 | Shiraishi et al. | 562/545 |
| 3,993,680 | 11/1976 | Grasselli et al. | 562/545 |
| 4,001,317 | 1/1977 | Grasselli et al. | 562/545 |
| 4,035,418 | 7/1977 | Okada et al. | 562/545 |

FOREIGN PATENT DOCUMENTS

| 2228538 | 12/1974 | France | 562/546 |
|---|---|---|---|
| 2303781 | 10/1976 | France | 562/546 |
| 4517659 | 2/1967 | Japan | 562/545 |

*Primary Examiner*—Vivian Garner
*Attorney, Agent, or Firm*—Charles S. Lynch; John E. Miller, Jr.; Larry W. Evans

[57] ABSTRACT

Iron-bismuth-molybdate catalysts further containing specific promoter elements have been found to exhibit excellent redox stability even under high stress conditions in the catalytic oxidation of olefins to unsaturated aldehydes and acids.

2 Claims, No Drawings

PROCESS FOR THE OXIDATION OF OLEFINS USING CATALYSTS CONTAINING VARIOUS PROMOTER ELEMENTS

This is a continuation of application Ser. No. 148,120 filed May 9, 1980 which is a continuation of parent application Ser. No. 819,733, filed July 9, 1977, both now abandoned.

BACKGROUND OF THE INVENTION

The process for oxidizing olefins by contacting the olefins together with an oxidizing agent with multicomponent catalysts is known. Grasselli and Hardman, in U.S. Pat. No. 3,642,930 disclose that certain complex catalysts based on iron, bismuth and molybdenum can be employed in the oxidation of olefins to obtain unsaturated aldehydes and acids. Also, see U.S. Pat. No. 4,001,317 and commonly assigned application Ser. No. 717,838, filed Aug. 26, 1976, now abandoned, the disclosure of which is incorporated herein by reference. Also see British Pat. No. 1,437,235, which discloses catalysts based on oxides of bismuth and molybdenum, which further contain at least one of indium, gallium, lanthanum and aluminum.

The catalysts described in these patents and applications are indeed very desirable for the oxidation of olefins to unsaturated aldehydes and acids. Unfortunately, some of these catalysts exhibit a less than desired redox stability when subjected to stressful conditions. More specifically, it occasionally happens in a commercial facility that the amount of oxygen fed to the reactor along with the olefin feed is either much greater or much less than the desired value. When this happens, it has been found that the catalysts may exhibit a significant decrease in catalytic activity. This, of course, is very disadvantageous.

Accordingly, it is an object of the present invention to provide a new process for the catalytic oxidation of olefins to unsaturated aldehydes and acids which employs catalysts having high redox stability so that the catalysts can withstand major deviations in redox conditions without significant decrease in catalytic activity.

SUMMARY OF THE INVENTION

This and other objects are accomplished by the present invention in accordance with which unsaturated aldehydes and acids are produced by the vapor phase oxidation of propylene or isobutylene with molecular oxygen at a temperature of about 200° to 600° C. in the presence of a catalyst represented by the following formula:

$$A_aB_bFe_cX_dM_eMo_{12}O_x$$

wherein
A is alkali metal, thallium, silver or mixtures thereof;
wherein
B is cobalt, nickel, zinc, cadmium, beryllium, calcium, strontium, barium, radium or mixtures thereof;
X is Bi, Te or mixtures thereof; and
wherein
M is selected from at least one of:
(1) Cr+W, Ge+W, Mn+Sb, Cr+P, Ge+P, Cu+W, Cu+Sn, Mn+Cr, Pr+W, Ce+W, Sn+Mn, Mn+Ge or combinations thereof;
(2) Cr, Sb, Ce, Pb, Ge, B, Sn, Cu or combinations thereof; and
(3) Mg+P, Mg+Cu, Mg+Cr, Mg+Cr+W, Mg+W, Mg+Sn, or combinations thereof; and further
wherein
$0 \leq a \leq 5, 0 \leq b \leq 20, 0 \leq c \leq 20, 0 \leq d \leq 20, 0.01 \leq e \leq 12$, and
x is a number such that the valence requirements for the other elements for oxygen are satisfied.

In one embodiment of the invention, the catalyst above-described is free of indium, gallium, lanthanum and aluminum when M is B, Cr, Cr+W, Sn, Pb, Ge and/or Cu.

In another embodiment, the catalyst as generically described above is free of indium, gallium, lanthanum and aluminum.

Preferably, the relative amounts of the various ingredients in the foregoing catalysts are such that the following inequalities apply: $0 \leq a \leq 0.5, 0.1 \leq b \leq 20, 0.1 \leq c \leq 20, 0.1 \leq d \leq 20$ and $0.01 \leq e \leq 6$.

The catalysts of this invention preferably contain K, Rb and/or Cs. Also, in the catalysts of the invention X is preferably Bi.

In a particularly preferred embodiment, the catalysts employed in the inventive process are represented by the formula:

$$A_aB_bFe_cBi_cM_eMo_{12}O_x$$

wherein
A is an alkali metal, preferably K, Rb, Cs or mixtures thereof;
B is Co, Ni or mixtures thereof; and
M is the same as described above; and further $0.03 \leq a \leq 0.5, 0.1 \leq b \leq 20, 0.1 \leq c \leq 20, 0.1 \leq d \leq 20$, and $0.1 \leq e \leq 6$.

These catalysts are preferably free of In, Ga, La and Al.

Of particular note are those catalysts falling within the foregoing generic descriptions in which M is selected from the group consisting of Cr+W, Ge+W, Cr+P, Ge+P, Cu+W, Cu+Sn, Mn+Cr, Sn+Mn, Mn+Ge, Pb, B, Sn and Mg+Sn.

In the foregoing generic descriptions in which the M component is a specific two-or-three-element system as described in subparagraphs (1) and (3), the minimum amount of each element in the system is 1, preferably 5, atom percent based on the total number of atoms in the system.

DETAILED DESCRIPTION

Processes for the oxidation of propylene and/or isobutylene to form the corresponding unsaturated aldehydes and acids are well known in the art. Broadly, a mixture of the olefin and molecular oxygen, optionally in the presence of steam or other diluent, is contacted with a catalyst at an elevated temperature of about 200° to 600° C. for a contact time sufficient to convert the olefin to the desired aldehydes and/or acids. Normally, the products of these reactions contains a very large portion of the aldehyde and a smaller byproduct amount of the unsaturated acid. The contact time may vary widely from a few seconds to ten or twenty seconds or more. The reaction can be conducted under atmospheric, superatmospheric or subatmospheric pressure with the use of a superatmospheric pressure normally being used on a commercial scale.

An important aspect of the present invention is the particular catalysts employed. The catalyst employed may be any of the catalysts delineated by the formula described above. Preferred are those catalysts falling within the foregoing generic description which contain potassium, rubidium, cesium or mixtures thereof and those which contain cobalt or nickel or mixtures thereof, and catalysts containing potassium, rubidium, cesium or mixtures thereof as well as nickel or cobalt or mixtures thereof are particularly preferred.

The catalysts of the present invention can be prepared by techniques well known in the art. In this connection, techniques for preparing analogous catalysts are thoroughly described in the patents and application referred to in the Background of the Invention. Such catalysts are most conveniently prepared by the coprecipitation of soluble salts, although any other conventional technique can be employed. More specific information on the preparation of catalysts is given in the following specific examples.

The catalysts of the present invention may be employed in unsupported form or they may be supported on a suitable carrier. Suitable carriers include silica, alumina, Alundum, titania, zirconia, silicon carbide and the like. The catalysts may also be used in various physical forms. For example, the catalysts can be employed in a form suitable for carrying out the inventive reaction in a fixed-bed mode or the catalyst can be employed in a form suitable for carrying out the invention reaction in a fluid-bed form.

As indicated above, a remarkable feature of the present invention is that the catalysts employed exhibit significant redox stability. In a commercial plant for producing unsaturated aldehydes and acids from propylene and isobutylene, mishaps inevitably occur. If the amount of molecular oxygen relative to the amount of olefin contacting the catalysts at any particular time significantly drops below the desired value, a noticeable decrease in catalytic activity of the catalyst may occur. In accordance with the present invention, the catalysts employed exhibit a far reduced tendency to lose their catalytic activity when subjected to unfavorable reaction conditions. From a commercial standpoint, therefore, the inventive process using the catalysts described herein has significant advantages over presently commercially practiced processes.

WORKING EXAMPLES

In order to more thoroughly illustrate the present invention, the following working examples are presented:

Various fixed-bed catalysts of the invention containing 20% $SiO_2$ were prepared by the procedures described below. Also prepared were a number of catalysts not included within the present invention, which were provided for comparative purposes.

Reference Catalyst A—80% $K_{0.1}Ni_{2.5}Co_{4.5}Fe_3BiP_{0.5}Mo_{12}O_x$ & 20% $SiO_2$ An aqueous slurry (referred to a solution A) containing 37.00 grams $(NH_4)_6Mo_7O_{24}.4H_2O$, 8.56 grams of a 0.10 g./ml. aqueous solution of $H_3PO_4$, 38 ml. of water and 25.43 grams of a 40% silica sol was prepared. An aqueous solution (referred to as solution B) containing 21.17 grams $Fe(NO_3)_3.9H_2O$, 8.47 grams $Bi(NO_3)_3.5H_2O$, 12.7 grams $Ni(NO_3)_2.6H_2O$, 22.87 grams $Co(NO_3)_2.6H_2O$ and 1.75 ml. of a 0.10 g./ml. aqueous solution of $KNO_3$ was separately prepared. Solution A was then heated initially to 45°–55° C. and solution B added dropwise to solution A with stirring. During addition of solution B, the temperature of the composition was increased so as to reach 75°–80° C. at the end of the solution B addition. Stirring was continued and the temperature of the composition maintained between about 80° and 85° C. until sufficient water had evaporated so that a thick paste was obtained.

The thick paste was placed in an oven at 120° C. and heated for about 2½ hours, the paste being stirred every ½ hour. Heating was then continued until the paste was dry. The dried paste was then heated in air at 290° C. for 3 hours and then at 425° C. for 3 hours. The heated paste was then additionally heated in air at 550° C. for 16 hours to produce the indicated catalyst.

Reference Catalyst B—80% $K_{0.1}Ni_{2.5}Co_{4.5}Fe_3BiW_{0.5}Mo_{12}O_x$ & 20% $SiO_2$ The procedure described above for the preparation of Reference Catalyst A was repeated except that an appropriate amount of $(NH_4)_6W_7O_{24}.6H_2O$ was substituted for the $H_3PO_4$ in solution A.

Catalysts 1 to 21

Catalysts having the general formula:

$$L_rK_{0.1}Ni_{2.5}Co_{4.5}Fe_qBiZ_{0.5}Mo_{12}$$ 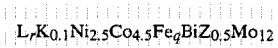

wherein
  L is Cr, Ge, Mn or Cu;
  Z is W, Sb, P, Sn, Cr, Cr, Pb, Ge or B; and
wherein
  q=2 or 3;
  r=0 or 1; and
  q+r=3
were prepared by the general method described above in connection with the preparation of Reference Catalyst A. These catalysts, which are composed of a base catalyst $K_{0.1}Ni_{2.5}Co_{4.5}BiMo_{12}O_x$ and a promoter system $Fe_qL_rZ_{0.5}$, are described in the following Table I. In this table, only the promoters are identified, the catalysts of course being composed of the identified promoters plus the base catalyst.

Oxidation of Propylene to Acrolein and Acrylic Acid

In order to illustrate the excellent redox stability of the catalysts of the present invention when employed in the inventive process, each of the catalysts described in Table I was subjected to a redox test in the following manner. 5 cc. of each catalyst prepared above was charged into a fixed-bed reactor. The temperature of the catalyst in the reactor was raised to a predetermined value and a feed comprising propylene/oxygen (in the form of air)/water in a ratio of ½.¾ was fed to the reactor at a rate such that the apparent contact time was 3 seconds and a WWH of about 0.07. Once the reaction had commenced, a sample of the product was recovered and analyzed for acrolein and acrylic acid so that the initial catalytic activity of the catalyst could be determined. Thereafter, the ratio of the ingredients in the feed as indicated above was changed to 1/0.7/4, and the temperature of the catalyst was raised to 400° C. This low oxygen feed was fed to the reactor under these conditions for a period of 2 hours. Next, the catalyst was reoxidized by feeding a feed of oxygen (in the form of air)/steam in a ratio of 2.3/4 to the catalyst at the reaction temperature indicated in Table I for 1 hour. Thereafter, the propylene flow was resumed to its initial value, and a product sample taken after the reaction had proceeded to steady state.

The results of these experiments are given in the following Table I. In this Table, the following definitions are used:

$$\% \text{ Per Pass Conversion} = \frac{\text{Moles of Propylene Reacted}}{\text{Moles of Propylene Fed}} \times 100$$

$$\% \text{ Selectivity} = \frac{\text{Moles of Product Formed}}{\text{Moles of Propylene Reacted}} \times 100$$

Performance Number = $\frac{1}{2}\{(PPC \text{ to } ACR. + AA) + (SEL. \text{ TO } ACR. + AA)\}$ In Table I, ACR is acrolein, and AA is acrylic acid. The performance number as defined above is a measure of the catalytic activity of a catalyst in that it is a function of both the selectivity and per pass conversion.

such modifications are intended to be included within the scope of the present invention, which is to be limited only by the following claims:

We claim:

1. In a process for the preparation of unsaturated aldehydes and acids from propylene or isobutylene by the vapor phase oxidation of propylene or isobutylene with molecular oxygen at a temperature of about 200° C. to 600° C. in the presence of a catalyst, the improvement comprising using as the catalyst a catalyst of the formula $$A_a B_b Fe_c Bi_d M_e Mo_{12} O_x$$

wherein
A is alkali metal, thallium, silver or mixtures thereof,
B is Ni and/or Co, and
M is Ge+W, and further

TABLE I

All Catalysts Supported on 20% SiO₂ (NALCO) Unless Stated Differently

| Example | Catalyst Promoter | Reaction Temp. °C. | Per Pass Conversion ACR | AA | ACR + AA | Selectivity ACR + AA | Performance No. Initial | Final | % Loss | % Improvement Over Reference Catalysts |
|---|---|---|---|---|---|---|---|---|---|---|
| (1) REFERENCE CATALYSTS | | | | | | | | | | |
| A | Fe₃P₀.₅ | 350 | 80.0 | 9.5 | 89.5 | 91.4 | 90 | 66 | −26.7 | — |
| A | Fe₃P₀.₅ | 350 | 79.0 | 9.4 | 88.4 | 90.7 | 90 | 72 | −20.0 | — |
| B | Fe₃W₀.₅ | 350 | 80.3 | 8.9 | 89.2 | 92.0 | 91 | 75 | −19.0 | +8.7 |
| (2) IMPROVED REDOX CATALYSTS | | | | | | | | | | |
| (A) Double Substituted | | | | | | | | | | |
| 1 | Fe₂CrW₀.₅ | 350 | 80.4 | 7.7 | 88.1 | 92.9 | 91 | 89 | −2.2 | +29.0 |
| 2 | Fe₂CrW₀.₅ | 380 | 75.1 | 15.4 | 90.5 | 93.1 | 92 | 90 | −2.2 | +30.4 |
| 3 | Fe₂GeW₀.₅ | 380 | 74.0 | 12.1 | 86.1 | 93.5 | 90 | 89 | −1.1 | +29.0 |
| 4 | Fe₂MnSb₀.₅ | 350 | 76.3 | 12.0 | 88.3 | 92.1 | 90 | 86 | −4.4 | +24.6 |
| 5 | Fe₂CrP₀.₅ | 380 | 76.0 | 10.8 | 86.8 | 90.0 | 88 | 84 | −4.5 | +21.7 |
| 6 | Fe₂CeP₀.₅ | 380 | 79.6 | 8.9 | 88.5 | 93.0 | 91 | 86 | −5.5 | +24.6 |
| 7 | Fe₂CuW₀.₅ | 320 | 75.2 | 2.9 | 78.1 | 96.9 | 87 | 81 | −6.9 | +17.4 |
| 8 | Fe₂CuW₀.₅ | 350 | 73.4 | 6.8 | 80.2 | 93.9 | 87 | 80 | −8.0 | +15.9 |
| 9 | Fe₂CuSn₀.₅ | 350 | 78.7 | 6.9 | 85.6 | 93.3 | 89 | 80 | −10.1 | +15.9 |
| 10 | Fe₂MnCr₀.₅ | 320 | 79.9 | 4.6 | 85.5 | 93.1 | 89 | 80 | −10.1 | +15.9 |
| 11 | Fe₂MnCr₀.₅ | 350 | 80.3 | 11.1 | 91.4 | 92.5 | 92 | 81 | −12.0 | +17.4 |
| 12 | Fe₂CrW₀.₅ | 320 | 83.2 | 6.4 | 89.6 | 92.8 | 91 | 81 | −11.0 | +17.4 |
| (B) Single Substituted | | | | | | | | | | |
| 13 | Fe₃Cr₀.₅ | 320 | 79.7 | 3.6 | 83.3 | 92.7 | 88 | 79 | −10.2 | +14.5 |
| 14 | Fe₃Sb₀.₅ | 320 | 74.7 | 10.8 | 85.5 | 88.0 | 87 | 80 | −8.0 | +15.9 |
| 15 | Fe₃Ce₀.₅ | 320 | 76.8 | 9.6 | 86.4 | 88.1 | 87 | 77 | −11.5 | +11.6 |
| 16 | Fe₃Pb₀.₅ | 320 | 76.6 | 4.3 | 80.9 | 89.1 | 85 | 74 | −12.9 | +7.3 |
| 17 | Fe₃Ge₀.₅ | 350 | 81.2 | 7.9 | 89.1 | 92.3 | 91 | 78 | −14.3 | +13.1 |
| 18 | Fe₃B₀.₅ | 350 | 79.1 | 11.8 | 90.9 | 90.9 | 91 | 79 | −13.2 | +14.5 |
| 19 | Fe₃Sn₀.₅ | 320 | 85.8 | 4.4 | 90.2 | 95.6 | 93 | 75 | −19.4 | +8.7 |
| (C) Mg—Containing Systems | | | | | | | | | | |
| 20 | Mg₇.₅Fe₃P₀.₅ | 380 | 71.0 | 6.9 | 77.9 | 91.1 | 84 | 86 | +2.4 | +24.6 |
| 21 | Mg₇.₅Fe₃.₅W₀.₅ | 380 | 64.5 | 4.4 | 68.9 | 95.6 | 82 | 83 | +1.2 | +20.3 |

From the foregoing, it can be seen that the catalysts of the present invention in the inventive reaction show a much smaller loss in performance number (and indeed some of the catalysts even show an improvement in performance number) over the reference catalysts. This means that the inventive catalysts when employed in the inventive reaction exhibit a far greater redox stability when subjected to unfavorable reaction conditions as compared to conventional catalysts.

Although only a few embodiments of the present invention have been described above, it should be appreciated that many modifications can be made without departing from the spirit and scope of the invention. All wherein
$0 \leq a \leq 0.5$, $0.1 \leq b \leq 20$, $0.1 \leq c \leq 20$, $0.1 \leq d \leq 20$ and $0.01 \leq e \leq 6$, and
x is a number such that the valence requirements for the other elements for oxygen are satisfied,
and wherein the minimum amount of each element in M is 1 atom percent based on the number of atoms in component M.

2. The process of claim 1 wherein A is K, Rb and/or Cs and wherein a is greater than 0.

* * * * *